United States Patent [19]

Traflet

[11] Patent Number: 4,795,442
[45] Date of Patent: Jan. 3, 1989

[54] MEDICAL TREATMENT TUBE CONSTRUCTION

[76] Inventor: Robert F. Traflet, 602 Washington Square S., #2207, Philadelphia, Pa. 19106

[21] Appl. No.: 96,117

[22] Filed: Sep. 11, 1987

[51] Int. Cl.⁴ ............................................. A61M 25/02
[52] U.S. Cl. ..................................... 604/179; 604/174
[58] Field of Search ............... 128/207.17, DIG. 26, 128/207.18, 207.14; 604/171, 172, 174, 178, 179, 180

[56] References Cited

U.S. PATENT DOCUMENTS

| | | | |
|---|---|---|---|
| 217,711 | 7/1879 | Shiland. | |
| 1,206,045 | 11/1916 | Smith. | |
| 1,610,793 | 12/1926 | Kaufman. | |
| 2,290,885 | 7/1942 | Lehmberg | 128/146 |
| 2,457,044 | 12/1948 | Hower | 128/148 |
| 2,468,383 | 4/1949 | Tiffany | 128/148 |
| 2,499,650 | 3/1950 | Kaslow | 128/148 |
| 2,663,297 | 12/1953 | Turnberg | 128/206 |
| 2,735,432 | 2/1956 | Hudson | 128/DIG. 26 X |
| 2,831,487 | 4/1958 | Tafilaw | 128/350 |
| 2,868,199 | 1/1959 | Hudson | 128/206 |
| 2,931,358 | 4/1960 | Sheridan | 128/206 |
| 3,161,199 | 12/1964 | Shaw | 128/348 |
| 3,253,594 | 5/1966 | Matthews et al. | 604/178 X |
| 3,648,703 | 3/1972 | Manker | 128/207.18 X |
| 3,972,321 | 8/1976 | Proctor | 604/179 |
| 4,167,946 | 9/1979 | Sandstrom | 128/207.17 |
| 4,175,564 | 11/1979 | Kwak | 604/171 |
| 4,363,323 | 12/1982 | Geiss | 604/281 |
| 4,658,814 | 4/1987 | Anderson | 604/179 X |

*Primary Examiner*—Gerald A. Michalsky
*Attorney, Agent, or Firm*—Dann, Dorfman, Herrell and Skillman

[57] ABSTRACT

A tube construction and, specifically, a nasogastric tube construction is provided for patient treatment. An elongated generally flexible tube of a selected diameter permits insertion of one end of the tube into a body orifice, such as the nasal cavity, of the patient. The flexible tube is of a selected length to extend from the body orifice to a remote connection. A tube sheath covers a predetermined portion of the tube adjacent to the body orifice. The tube sheath has one end positioned adjacent the body orifice and is of sufficient length to extend from the body orifice to a position along the tube generally beyond the normal reach of the patient. Fastening straps affixed to the tube sheath anchor the tube sheath to the patient so that an end of the tube sheath is held in position adjacent the body orifice to prevent patient access to the tube covered by the sheath. The fastening straps are inelastic to prevent the patient from pulling the tube sheath away from the orifice and gaining access to the portion of the tube proximate the orifice. The tube sheath and fastening straps prevent removal of the tube by the patient.

20 Claims, 1 Drawing Sheet

MEDICAL TREATMENT TUBE CONSTRUCTION

FIELD OF THE INVENTION

The present invention relates to a tube construction for patient treatment and, more particularly, to a nasogastric tube construction which renders difficult the removal of a functional nasogastric tube while at the same time not substantially further incumbering the patient.

BACKGROUND OF THE INVENTION

During the treatment of patients, it is often necessary to insert various types of tubes into body orifices, such as the nose. Because an inserted tube often feels very uncomfortable, patients frequently attempt to remove the tubes during treatment. To limit the risk of patient interference with medical treatment, various devices and methods have been employed in an attempt to deter the removal of the tubes by the patient.

In conventional application, nasogastric tubes have been inserted through the nose and nasal cavity of a patient down the esophagus and into the stomach as needed in connection with patient treatment. In order to prevent the patient from removing the nasogastric tube once it has been inserted, the tube has frequently been taped in place to the face of the patient. Unfortunately, such an arrangement usually only adds to the discomfort of the patient while providing little impediment to the removal of the tube by the patient.

In other arrangements, elastic headbands have been employed to hold the nasogastric tube in position. While relieving patient discomfort caused by the conventional use of tape, elastic headbands also offer only marginal protection against patient removal of the tube. In some arrangements, a patient can grasp the tube beyond the holder to pull it from the nose. In other arrangements, the elasticity of the headband itself permits the tube holder to be pulled away from the face to expose the tube thereby enabling a patient to grasp the tube and pull it from the nose.

In accordance with the present invention, a tube construction is provided which effectively holds a nasogastric tube in position without imposing any additional undue discomfort to the patient. The tube construction, in accordance with the present invention, overcomes many of the deficiencies of the conventional arrangements by effectively and efficiently preventing the removal of a nasogastric tube by the patient.

SUMMARY OF THE INVENTION

The present invention provides a means of impeding a patient from removing a treatment tube from a body orifice during treatment, and in specific, application provides a means of impeding the patient from pulling a nasogastric tube out of the patient's nose and stomach to relieve the discomfort caused by the inserted tube. The medical treatment tube construction in accordance with the present invention provides a means of limiting the access of the patient to a functional treatment tube while at the same time providing a minimum of annoying incumberance to the patient.

More specifically, a tube construction for patient treatment is provided which includes an elongated, generally flexible tube of a selected diameter to permit insertion of one end of the tube into a body orifice of a patient. The tube is of a selected length to extend from the body orifice to a remote connection, such as a medical treatment device. The generally flexible tube may, for example, be in the form of a nasogastric tube which is inserted into the patient's nose and nasal cavity.

In order to prevent the removal of the tube by a patient, a tube sheath is employed to cover a predetermined portion of the tube adjacent to the body orifice into which the tube is inserted. One end of the tube sheath is positioned adjacent to the body orifice of the patient, and the tube sheath is of a sufficient length to extend from the body orifice to a position along the tube generally beyond the normal pulling reach of the patient. The tube sheath is generally non-retractable over the portion of the tube covered by the sheath in order to deny patient access to the tube.

Sheath holder means anchors the tube sheath to the patient so that the appropriate end of the tube sheath is held in position adjacent to the body orifice to prevent patient access to the tube covered by the tube sheath. The sheath holder means prevents the patient from pulling the tube sheath away from the orifice and gaining access to the portion of the tube proximate the orifice. As such, removal of the tube by the patient is prevented.

DESCRIPTION OF THE DRAWINGS

The foregoing summary, as well as the following detailed description of the preferred embodiment of the present invention will be better understood when read in conjunction with the appended drawings in which.

DESCRIPTION OF THE PREFERRED EMBODIMENT

Figure 1:
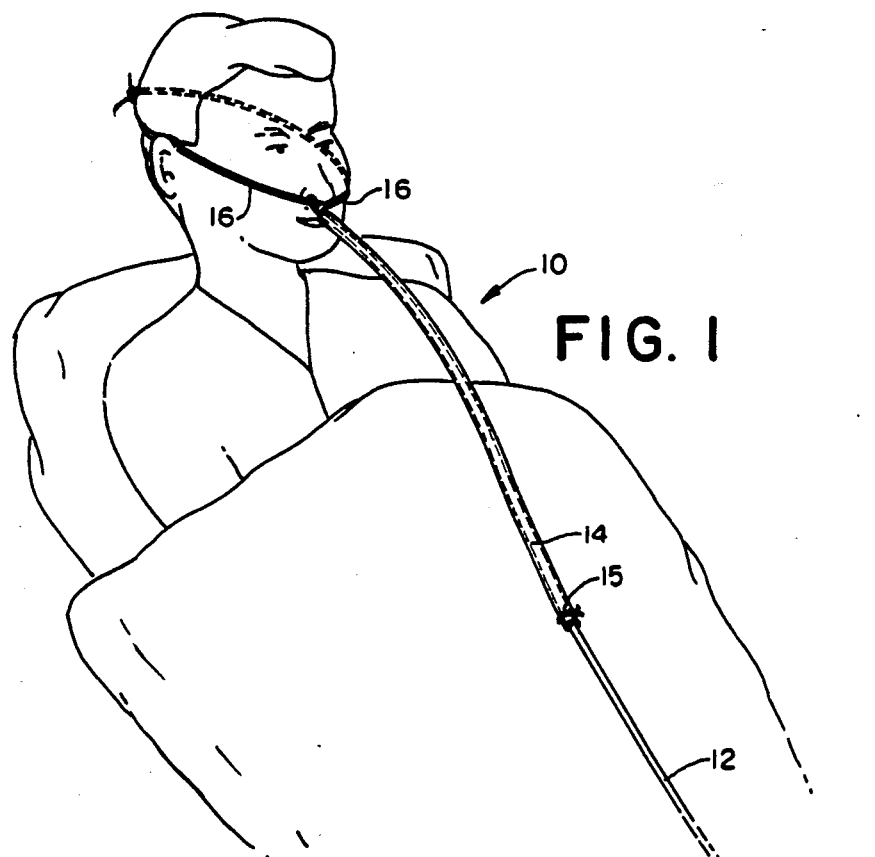
FIG. 1 is a perspective view showing a patient having a nasogastric tube inserted into the nose with a tube sheath and fastening straps holding the nasogastric tube in position.
Figure 2:
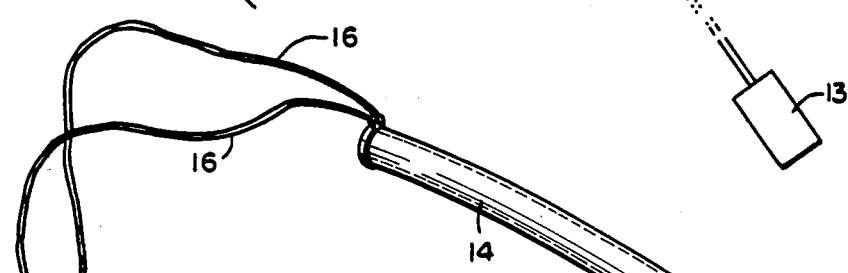
FIG. 2 is a perspective view of a tube sheath and fastening straps when removed from the nasogastric tube and the patient.

Referring to FIG. 1, a patient 10 is depicted in bed with an elongated generally flexible medical treatment tube 12 in position for patient treatment. For this purpose, the treatment tube 12 is of a selected length to extend from a remote connection, such as a medical treatment apparatus 13, into a body orifice of the patient. As shown, the medical treatment tube 12 is in the form of a nasogastric tube, which is inserted through the patient's nose and nasal cavity through the esophagus and into the patient's stomach. The nasogastric tube 12 is of a predetermined diameter and is sufficiently flexible to make the bends and curves needed to allow the tube to be properly inserted into the patient.

In accordance with the present invention, a tube sheath 14 which may, for example, be constructed for use in different applications as either a rigid, semi-rigid or even a flexible piece, is provided for covering a predetermined portion of the tube adjacent the patient's nose. The tube sheath has a generally annular cross-section with an inner diameter slightly larger than the outer diameter of the treatment tube. The tube sheath 14 is dimensioned to slide into position over the treatment tube 12 so that one end of the sheath may be positioned adjacent the body orifice, such as the patient's nose. The length of the tube sheath 14 is at least on the order of two feet and may be longer in order to prevent the patient from reaching the functional tube 12 when the tube sheath is pulled into place against the nose of the patient. In general, the tube sheath 14 should have a sufficient length to extend from the patient's nose to a position along the tube generally beyond the normal pulling reach of the patient. While the patient may still be able to touch or even hold the exposed portion of the tube 12 beyond the end of the sheath 14 distal to the body orifice, the sheath 14 must be sufficiently long to prevent the patient from being able to grasp the tube at a close enough distance or proximity to the patient's body to enable the patient to pull the tube out of the body orifice.

In order to hold the sheath 14 in place, fastening members in the form of at least two straps 16 are provided to anchor the tube sheath to the patient so that the appropriate end of the tube sheath is held in position adjacent the body orifice, such as the nose. The straps 16 may be affixed at or near the end of the tube sheath 14 in any suitable manner. To place the tube sheath in proper position, the fastening straps 16 may be pulled together around the patient's head in order to force the end of the tube sheath to which the straps are attached against the nose or face of the patient. To secure the tube sheath 14 in proper position, the straps 16 may then be fastened or tied together behind the patient's head.

The fastening straps 16 are preferably inelastic in order to prevent the patient from gaining access to the tube by pulling the tube sheath away from the orifice against the elasticity of the straps. The inelasticity of the straps 16 prevents the patient from gaining access to the portion of the tube 12 proximate the orifice and thereby prevents the patient from grasping the tube at that location and removing it from the orifice.

To further deny patient access to the portion of the tube 12 covered by the sheath 14, it is desirable for the sheath 14 to have positional retention means to prevent the sheath from being retractable by the patient over the portion of the tube covered by the sheath. For this purpose, the sheath 14 may in certain applications be constructed of a suitable compositional structure resistant to axial compression to prevent the patient from being able to expose the covered portion of the tube 12 by gathering or compressing the sheath together in an axial direction along the tube toward the patient. To this end, the sheath 14 may be formed as a rigid member from a compositional material such as a metal or a rigid, dimensionally stable synthetic resinous material or a plastic material derived therefrom, to prevent any axial or radial compression of the sheath. Alternatively, the sheath may be formed as a semi-rigid member from a compositional material such as a chemically stable synthetic resinous material, or a plastic material derived therefrom, such as a polyvinyl or acrylic resin or plastic to prevent or resist axial compression while permitting the sheath to be flexible enough to bend. A non-retractable sheath 14 prevents the patient from exposing any significant amount of the covered portion of the tube at a close enough distance or proximity to the patient to enable the patient to grasp and pull the tube from the body orifice.

In certain applications, the sheath may desirably be constructed as a rigid structure to prevent the sheath and, therefore, the tube within the sheath from being bent by the patient. A rigid sheath also serves as positional retention means to deny patient access to the tube by preventing the patient from bending the sheath to reach the exposed portion of the tube beyond the distal end of the sheath.

As either alternative or additional positional retention means, the sheath may include a fastener for securing the sheath 14 to the tube 12 at a selected position along the sheath distal to the body orifice. As shown in FIG. 1, the fastener may be in the form of a tie 15 for tying around the sheath and the tube at a position generally beyond the reach of the patient t tightly hold the sheath in position on the tube. The tie 15 may be removable from the sheath to permit the tie to be positioned or repositioned at different locations along the sheath.

Figure 3:
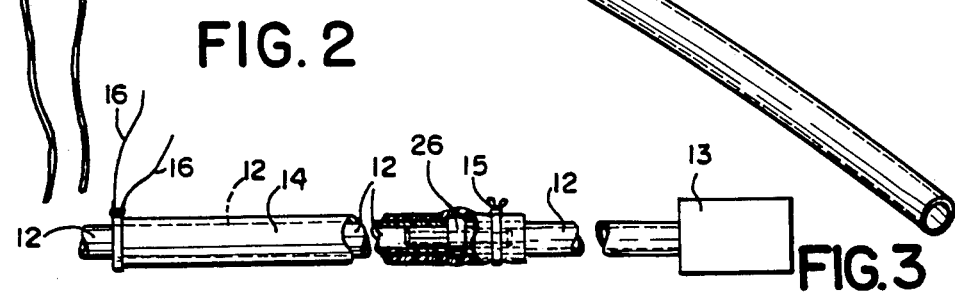
FIG. 3 is a side view, partially cut away, of a tube sheath in use over a nasogastric tube having an enlarged diameter portion formed by a tube coupling member in which a tie for the sheath is used in conjunction with the enlarged diameter portion of the tube to hold the sheath in position.

As shown in FIG. 3, the body treatment tube 12 may include a coupling member 26 for coupling the portion of the tube from the patient with a portion of the tube from the remote connection 13, such as a medical treatment apparatus. Generally, the coupling member 26 provides an enlarged diameter portion along the tube intermediate the body orifice of the patient and the remote connection Conveniently, the enlarged diameter portion of the tube may be used in conjunction with the tie 15 to further prevent the retraction of the sheath over the tube by the patient. This may be accomplished by positioning the tie 15 along the sheath at a location between the enlarged portion of the tube formed by the coupling member 26 and the remote connection 15. When properly tied in position, the tie will not slip or pass over the enlarged portion of the tube if the patient attempts to pull the sheath over the tube toward the patient. In this arrangement, a semi-rigid or a non-rigid, flexible sheath constructed from a cloth or reinforced cloth material, for example, should be employed to enable the sheath to be slipped over the enlarged portion of the tube and constricted about the tube by the tie 15. The tie 22 functions to constrict the sheath to a diameter smaller than the enlarged diameter of the tube to stop any movement of the tie over the enlarged portion of the tube. This effectively prevents the patient from pulling the sheath over the tube to gain access to the exposed portion of the tube at a short enough distance to the body orifice to permit the patient to pull the tube from the body orifice.

When placed into proper position, the sheath 14 and fastening straps 16 effectively prevent the patient from removing a functional tube 12. The length of the sheath 14 prevents the patient from pulling the tube 12 from a location beyond the end of the sheath distal to the body orifice, and the inelasticity of the fastening straps 16 prevents the patient from gaining access and pulling the tube 12 from a location proximate the body orifice. Additionally, if the patient grasps the sheath and attempts to pull, the inelasticity of the fastening straps 16 will prevent any significant movement of the sheath away from the face and will also prevent any significant removal of the tube from the body orifice.

From the foregoing description and the accompanying drawings, it can be seen that the present invention provides a tube construction for medical treatment which is both easy and effective to use. It can be recognized by those skilled in the art that changes or modifications may be made to the above-described embodiment within the scope and spirit of the invention as defined by the appended claims.

What is claimed is:

1. A tube construction for patient treatment comprising:
    an elongated generally flexible tube of a selected diameter to permit insertion of one end into a body orifice of a patient and of a selected length to extend from the body orifice to a remote connection;
    a tube sheath for covering a predetermined portion of the tube adjacent said body orifice, the tube sheath having one end to be positioned adjacent the body orifice of the patient and a sufficient length to extend from the body orifice to a position along the tube generally beyond the normal reach of the patient, the tube sheath having retention means to prevent the sheath from being retractable over the portion of the tube covered by the sheath to deny patient access to the tube; and
    sheath holder means for anchoring the tube sheath to the patient so that the end of the tube sheath is held in position adjacent the body orifice to prevent patient access to the tube covered by said sheath, said holder means being inextensible so that when the holder is in position on the patient, it prevents the patient from pulling the tube sheath away from the orifice and gaining access to the portion of the tube proximate the orifice in order to prevent dislodgement of the tube by the patient.

2. The tube construction of claim 1 in which the sheath holder means comprises two elongated generally inelastic fastening members fixed to the sheath so that the fastening members may be secured together around a portion of the patient's body to hold the sheath in position.

3. The tube construction of claim 2 in which the two members are of a length to extend around the patient, so that the ends may be tied together at a position remote from said body orifice.

4. The tube construction of claim 1 in which the tube sheath comprises cloth material.

5. The tube construction of claim 1 wherein said tube is a nasogastric tube and said body orifice is said nose.

6. The tube construction of claim 5 wherein said sheath holder means comprises two elongated generally inelastic fastening members fixed to the sheath and having a length so that the fastening members may be secured together generally behind the patient's head to hold the sheath in position extending outwardly from the nose of the patient away from the patient's face.

7. The tube construction of claim 1 in which said retention means comprises a compositional structure of the sheath.

8. The tube construction of claim 7 in which the compositional structure is a semi-rigid material.

9. The tube construction of claim 8 in which said semi-rigid material comprises a synthetic resinous material.

10. The tube construction of claim 9 in which said semi-rigid material comprises a plastic material derived from the synthetic resinous material.

11. The tube construction of claim 7 in which said retention means comprises a fastener for securing the sheath to the tube at a selected position along said sheath distal to the body orifice.

12. The tube construction of claim 11 in which said selected position along said sheath is beyond the normal reach of the patient.

13. The tube construction of claim 11 in which said tube has an enlarged diameter portion disposed intermediate the remote connection and the body orifice, and said selected position along said sheath for said fastener is between said enlarged diameter portion and said remote connection.

14. The tube connection of claim 11 in which said fastener is a tie for tying around the sheath and tube.

15. The tube construction of claim 1 in which said retention means comprises a fastener for securing the sheath to the tube at a selected position along said sheath distal to the body orifice.

16. The tube construction of claim 15 in which said selected position along said sheath is beyond the normal reach of the patient.

17. The tube construction of claim 15 in which said tube has an enlarged diameter portion disposed intermediate the remote connection and the body orifice, and said selected position along said sheath for said fastener is between said enlarged diameter portion and said remote connection.

18. The tube construction of claim 15 in which said fastener is a tie for tying around the sheath and tube.

19. The tube construction of claim 1 in which the retention means prevents the patient from bending the sheath to gain access to the tube.

20. The tube construction of claim 19 in which said retention means comprises a rigid compositional structure of the sheath.

* * * * *

UNITED STATES PATENT AND TRADEMARK OFFICE
CERTIFICATE OF CORRECTION

PATENT NO. : 4,795,442
DATED : January 3, 1989
INVENTOR(S) : Robert F. Traflet, M.D.

It is certified that error appears in the above-identified patent and that said Letters Patent is hereby corrected as shown below:

Column 4, line 12, after "patient" and before "tightly", "t" should be --to--;

Column 4, line 23, after "connection", insert --.-- (period);

Column 5, line 46, after "in" insert --a--;

Signed and Sealed this

First Day of August, 1989

Attest:

DONALD J. QUIGG

Attesting Officer

Commissioner of Patents and Trademarks